United States Patent [19]
Daignault, Jr. et al.

[11] Patent Number: 6,053,905
[45] Date of Patent: Apr. 25, 2000

[54] SELF CONTAINED URETHRAL CATHETER ASSEMBLY WITH LUBRICATING CHAMBER

[75] Inventors: Kenneth J. Daignault, Jr., Jefferson; Donald A. Coelho, Jr., Bellingham; Lee C. Burnes, North Attleboro; James A. Walls, Sharon, all of Mass.

[73] Assignee: Tyco International (US) Inc., Exeter, N.H.

[21] Appl. No.: 09/027,678

[22] Filed: Feb. 23, 1998

[51] Int. Cl.⁷ .................................................. A61M 27/00
[52] U.S. Cl. .......................... 604/544; 604/331; 604/349; 206/364; 206/571
[58] Field of Search ..................... 604/265, 328, 604/331, 349, 544; 206/364, 571

[56] References Cited

U.S. PATENT DOCUMENTS

| | | |
|---|---|---|
| 3,854,483 | 12/1974 | Powers . |
| 3,934,721 | 1/1976 | Juster et al. ............................. 206/364 |
| 3,967,728 | 7/1976 | Gordon et al. .......................... 206/364 |
| 4,230,115 | 10/1980 | Walz, Jr. et al. . |
| 4,652,259 | 3/1987 | O'Neil . |
| 4,811,847 | 3/1989 | Reif et al. ................................ 206/571 |
| 5,147,341 | 9/1992 | Starke et al. . |
| 5,226,530 | 7/1993 | Golden ..................................... 206/364 |
| 5,242,398 | 9/1993 | Knoll et al. .............................. 604/544 |
| 5,454,798 | 10/1995 | Kubalak et al. ......................... 604/328 |
| 5,501,341 | 3/1996 | Vanes ....................................... 206/364 |

FOREIGN PATENT DOCUMENTS

| | | |
|---|---|---|
| 1493257 | 11/1977 | United Kingdom . |
| 94/06377 | 3/1994 | WIPO .................................... 604/328 |
| WO 98/06642 | 2/1998 | WIPO . |

*Primary Examiner*—Mark O. Polutta
*Attorney, Agent, or Firm*—Weingarten, Schurgin, Gagnebin & Hayes LLP

[57] ABSTRACT

A self-contained, self-lubricating catheter assembly is provided. A receptacle formed of two opposed flexible walls includes a main chamber and a lubrication chamber separated by a passage. A lubricant is provided in the lubrication chamber. A catheter is advanced from the main chamber through the lubrication chamber and picks up lubricant as it is passes through the lubrication chamber. A catheter grasping mechanism, located proximate the exit from the lubrication chamber, permits advancement of the catheter out of the receptacle and resists movement of the catheter back into the receptacle. The receptacle also includes one or more finger holes therethrough to allow the user to retain the receptacle on one or more fingers, thereby allowing the hand to more readily position the receptacle during use while advancing the catheter.

38 Claims, 7 Drawing Sheets

SELF CONTAINED URETHRAL CATHETER ASSEMBLY WITH LUBRICATING CHAMBER

BACKGROUND OF THE INVENTION

Pre-lubricated, self-contained urinary catheters are useful to provide a cleaner, less time consuming procedure. Catheter handling is reduced, as well as the risk of infection. Generally, self-contained catheters are contained within a flexible receptacle which serves to store the catheter before use and collects the urine during use of the catheter. An introducer, provided at an exit of the receptacle, aids introduction of the catheter into the urethra. The catheter is precoated with a lubricant, which eliminates the need for manual lubrication of the catheter by a user and, since the lubricated catheter is contained within the receptacle until use, incidental contact between the lubricant and the user is minimized.

In use, the distal end of the catheter is introduced into the urethra using the introducer. The catheter is advanced by gripping the catheter through the receptacle and moving the catheter with one hand until the hand reaches the top of the receptacle. The catheter is held in this position with the other hand while the receptacle is straightened out. Then the catheter is advanced another distance. The user proceeds in this manner until the catheter reaches the bladder and urine starts to flow.

A disadvantage of such a prelubricated, self-contained catheter is that the lubricant can become dispersed over the interior of the receptacle, causing the walls of the receptacle to stick together. This can make it difficult to advance the catheter and wastes lubricant. Additionally, it can be difficult to hold the receptacle and guide the catheter at the same time, particularly if a patient is attempting self-catheterization.

BRIEF SUMMARY OF THE INVENTION

The present invention provides a self-contained, self-lubricating catheter assembly having a receptacle containing a catheter. The receptacle is formed of two opposed flexible walls extending from a distal end to a proximal end. A main chamber and a lubrication chamber are formed between the flexible walls. A passage separates the main chamber and the lubrication chamber, and an exit from the lubrication chamber is formed in the distal end of the receptacle. A lubricating material or lubricant is provided in the lubrication chamber. As the catheter is advanced through the lubrication chamber, it picks up lubricant.

A catheter grasping mechanism is located proximate to and preferably within the exit. The catheter grasping mechanism has a passageway therethrough sized to allow the catheter to pass through. The user can grasp and hold the catheter by squeezing the grasping mechanism with the fingers to retain the catheter in an advanced position. Alternatively, a catheter engaging device may extend partially into the passageway of the grasping mechanism and be configured to permit advancement of the catheter out of the receptacle and resist movement of the catheter back into the receptacle. For example, the catheter engaging device may comprise tabs extending radially inwardly and distally from walls of the passageway. Inwardly extending protrusions or a user-accessible dial with external teeth to engage the catheter may also be provided.

The receptacle may also include one or more finger holes extending therethrough to allow the user to retain the receptacle on one or more fingers, thereby freeing the hand to more easily position the receptacle adjacent to the opening of the urethra while advancing the catheter.

In use, the user grips the catheter through the receptacle walls and directs it through the lubrication chamber and out the exit. The catheter is advanced by pushing it from the proximal end of the lubrication chamber. When the proximal end of the lubrication chamber reaches the distal end, the user grasps the catheter through the grasping mechanism, lubrication chamber or introducer with a free hand to retain the catheter in the advanced position and straightens out the receptacle with the other hand. Once the receptacle has been straightened out, the user grips the catheter through the walls of the receptacle again and advances it another distance in the same manner.

In this way, the catheter assembly is readily held and used. The lubricant is not smeared within the main chamber of the receptacle. Thus, the walls in the main chamber of the receptacle do not stick together, and the catheter can be more readily gripped and advanced through the walls. Also, less lubricant is wasted. The finger holes allow a user to more readily position the receptacle and retain and guide the catheter at the same time, which is particularly useful for patients who must catheterize themselves.

BRIEF DESCRIPTION OF THE DRAWINGS

The invention will be more fully understood from the following detailed description taken in conjunction with the accompanying drawings in which.

DETAILED DESCRIPTION OF THE INVENTION

Figure 1:
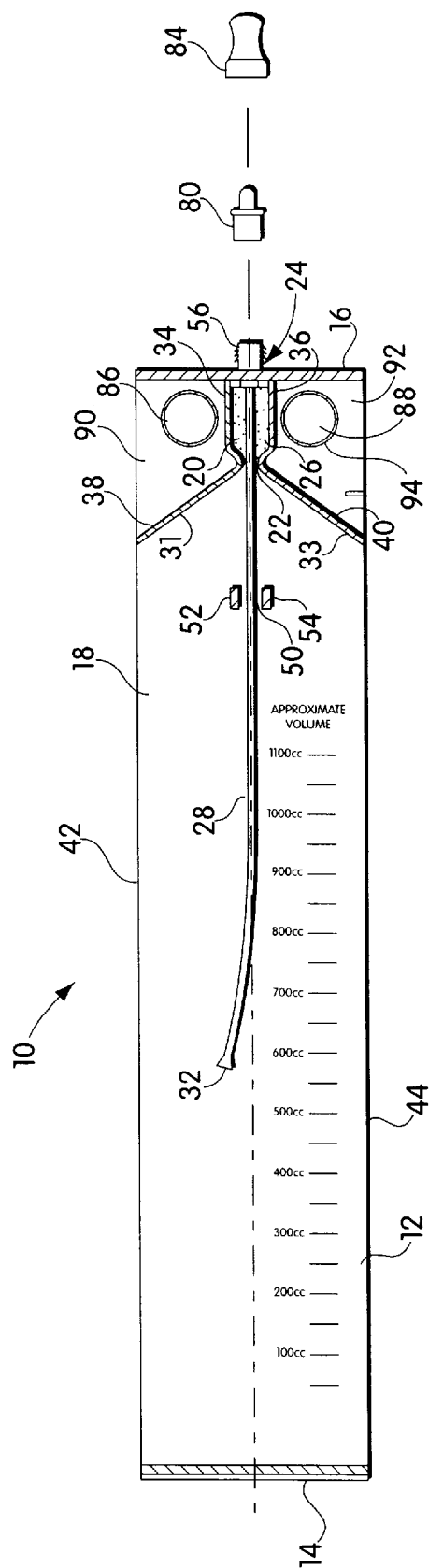
FIG. 1 is a schematic exploded view of a catheter assembly according to the present invention.

Referring to FIG. 1, a catheter assembly 10 according to the present invention includes a receptacle 12 having flexible walls made from an extruded or sheet material and extending from a proximal end 14 to a distal end 16. The receptacle includes a main chamber 18 adjacent the proximal end 14 and a lubrication chamber 20 adjacent the distal end 16 of the receptacle 12. A passage 22 separates the lubrication chamber 20 from the main chamber 18. A distal opening 24 from the lubrication chamber 20 forms an exit in the distal end 16 of the receptacle 12.

The lubrication chamber 20 contains a lubricating gel or lubricant 26. Any suitable medical lubricating gel known in the art can be used. The passage 22 between the lubrication chamber 20 and the main chamber 18 is sufficiently narrow to minimize migration of the lubricant into the main chamber. In an alternative embodiment, a valve assembly 27, shown in FIG. 9, can be located within the passage 22 to further minimize migration of the lubricant.

A catheter 28 is disposed within the receptacle 12. The catheter is typically either a red rubber or a vinyl catheter, as is known in the art. During storage, the catheter is retained in the main chamber 18. During use, a user grasps the catheter through the flexible walls of the receptacle and threads the distal end 30 (see FIG. 10) of the catheter 28 through the passage 22 into the lubrication chamber 20 and out the exit 24. The proximal end 32 of the catheter may be widened or may include a retention device thereon to prevent the catheter from being pulled entirely out of the main chamber.

In the embodiment illustrated in FIG. 1, the receptacle 12 is formed from an extruded material such as a polyethylene which is supplied as a tube cut to a suitable length and sealed at the proximal and distal ends 14, 16. Alternatively, the receptacle could be formed of one or more sheets of a flexible material sealed along seams extending between the proximal and distal ends. The seals at the proximal and distal ends and the seams extending between the ends may be formed in any suitable manner, such as by heat sealing, adhesive, stitching, RF welding, impulse welding, or chemical bonding. Other embodiments are possible. For example, a sheet of a flexible material could be folded to form the proximal end 14 and sealed at the distal end and along sides extending between the proximal and distal ends.

The lubrication chamber 20 and the distal end of the main chamber are defined by bond lines 31, 33 which seal opposed walls of the receptacle together. The lubrication chamber is formed by the bond line portions 34, 36 of bond lines 31, 33 respectively extending generally parallel from the distal end 16 of the receptacle 12. The bond lines converge at the proximal end of the lubrication chamber 20 to define the passage 22 between the lubrication chamber 20 and the main chamber 18. Bond line portions 38, 40 of bond lines 31, 33 respectively then diverge from the passage 22 toward the sides 42, 44 of the receptacle to form the distal end of the main chamber.

Figure 9:
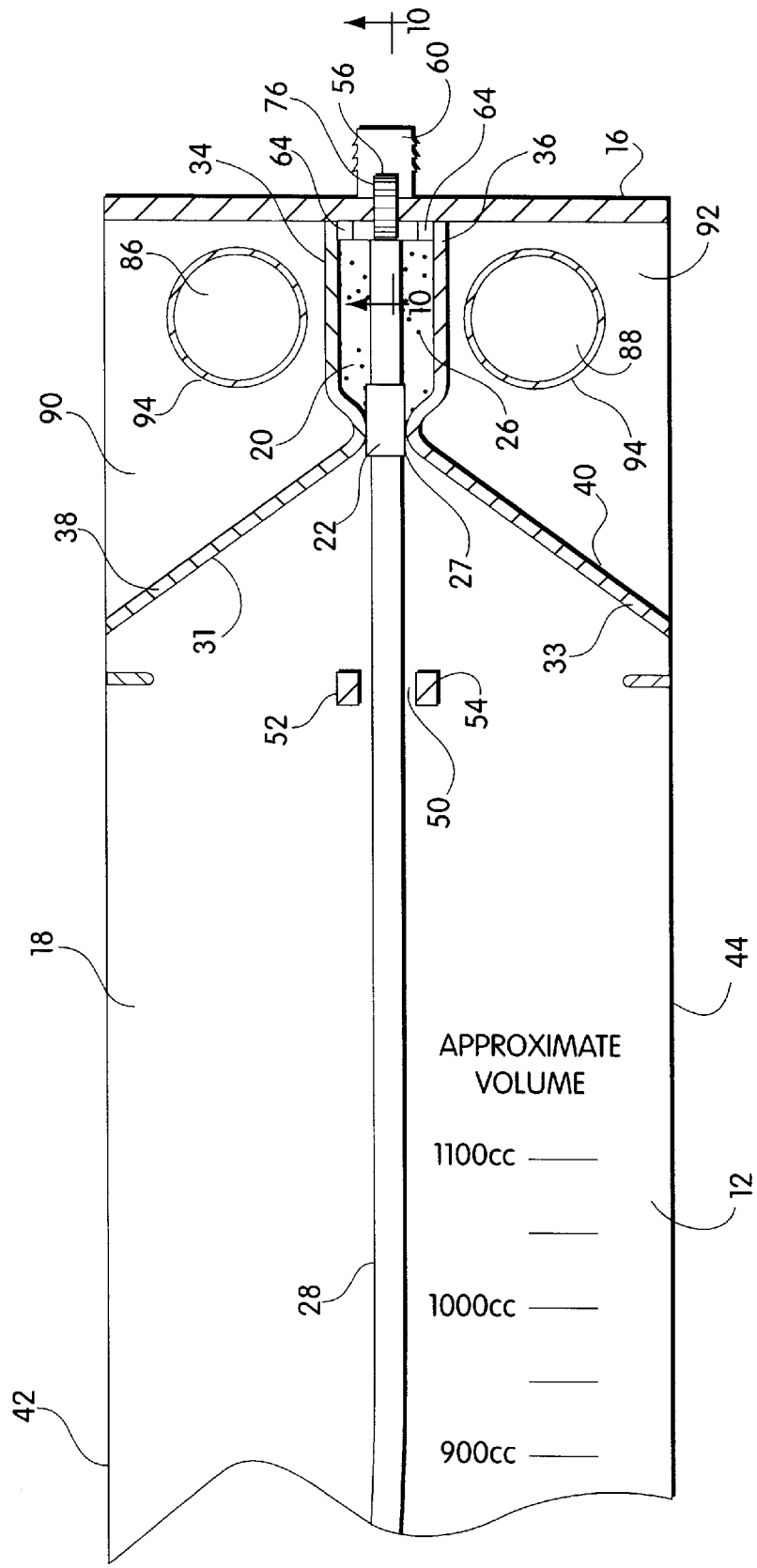
FIG. 9 is a partial plan view of a catheter assembly illustrating a further embodiment of a catheter grasping mechanism.

Preferably the diverging bond line portions 38, 40 extend at an acute angle from the passage 22 toward the sides 42, 44 of the receptacle 12 to form a catheter guideway as illustrated in FIGS. 1 and 9. This angle aids the user in guiding the distal end 30 of the catheter 28 toward the passage 22 to the lubrication chamber 20. However, the diverging bond line portions 38, 40 may also extend directly toward the sides 42, 44, i.e., parallel to the proximal and distal ends 14, 16 of the receptacle, if desired.

Preferably, a catheter guide channel 50 is also provided in the main chamber, which also functions as a catheter guideway. The guide channel is formed by a pair of short parallel bond lines 52, 54 sealing the opposed walls of the receptacle in a central region of the main chamber 18 and spaced from the passage 22 to the lubrication chamber 20. The guide channel 50 aids in locating the catheter 28 centrally within the main chamber, which is helpful when the user is directing the catheter into and through the lubrication chamber. The guide channel can also be used to hold the catheter outside of the lubrication chamber 20 prior to using the catheter. The bond lines defining the lubrication chamber, the distal end of the main chamber, and the catheter guide channel can be formed in any suitable manner, such as by heat sealing, adhesive, stitching, RF welding, or impulse welding. In an alternative embodiment, the lubrication chamber can be provided as a separate component, such as a suitably sized bag or bladder sealed within the receptacle adjacent the exit 24; an opening on one end of the bag defines the passage 22 from the main chamber and another opening is located adjacent the exit 24.

Figure 2:
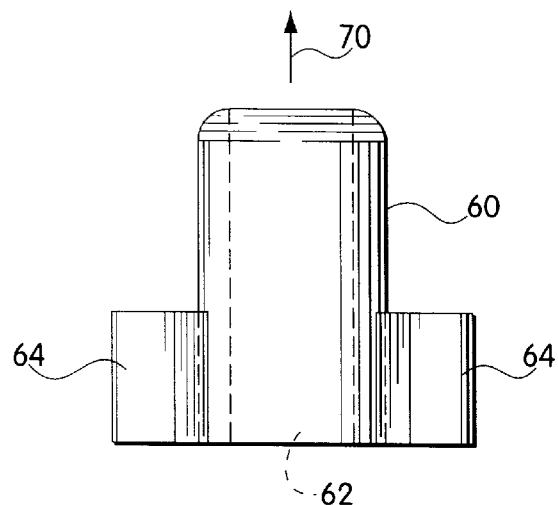
FIG. 2 is a side view of a catheter grasping mechanism according to the present invention.
Figure 3:
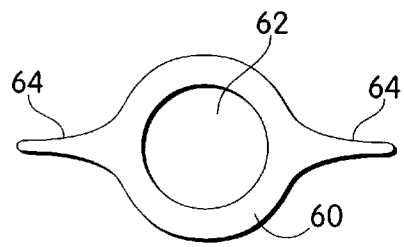
FIG. 3 is a plan view of the catheter grasping mechanism of FIG. 2.
Figure 4:
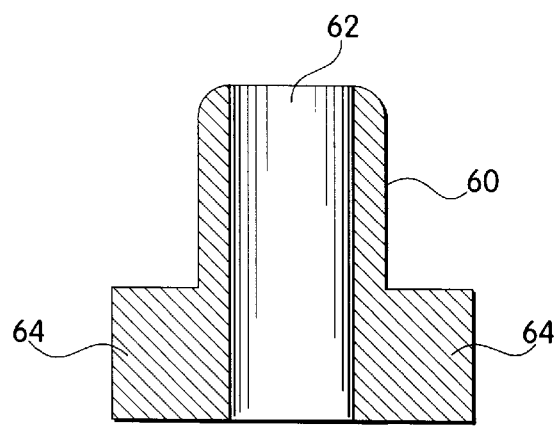
FIG. 4 is a cross-sectional view of the catheter grasping mechanism of FIG. 2.

A catheter grasping mechanism 56 is located proximate and preferably within the exit 24 from the lubrication chamber 20 to permit advancement of the catheter 28 out of the receptacle 12 and resist slippage of the catheter back into the receptacle. Referring to FIGS. 2–4, the grasping mechanism comprises an insert 60 having a passageway 62 therethrough. The insert is fixedly located within the exit 24 in any suitable manner. For example, the insert may include flanges or wings 64 protruding from opposed sides thereof and which are fixed, such as by heat sealing, within the bond line portions 34, 36 at the distal end of the lubrication chamber and within the bond line at the distal end 16 of the receptacle. Preferably, the insert is formed of the same material as the receptacle (for example, polyethylene) to assist in bonding thereto. The insert may be fixed proximate the exit of the receptacle in any other suitable manner, as would be known in the art. Preferably, the protrusion of the insert into the lubrication chamber is minimized to provide additional space for the lubricant therein. In use, the user can grasp and hold the catheter by squeezing the grasping mechanism with the fingers to retain the catheter in an advanced position or by squeezing the catheter through the lubrication chamber.

Figure 5:
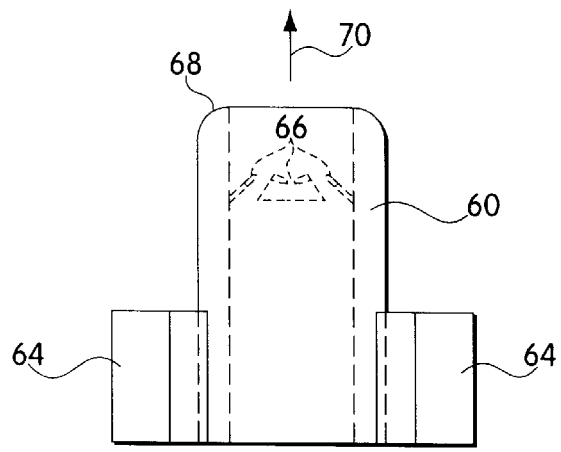
FIG. 5 is a side view of a further embodiment of a catheter grasping mechanism according to the present invention.
Figure 6:
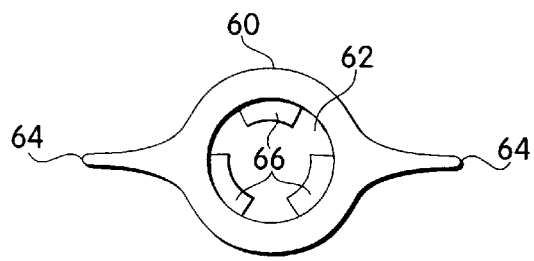
FIG. 6 is a plan view of the catheter grasping mechanism of FIG. 5.
Figure 7:
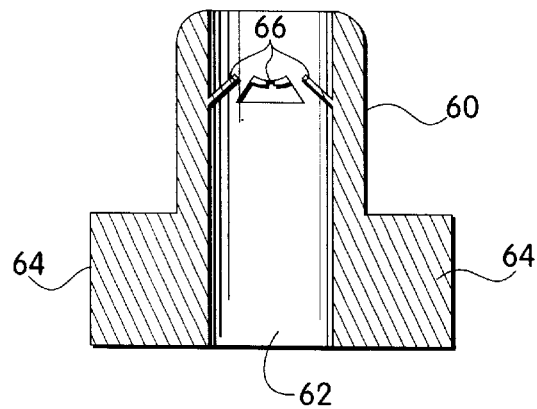
FIG. 7 is a cross-sectional view of the catheter grasping mechanism of FIG. 5.

In another embodiment, illustrated in FIGS. 5–7, the catheter grasping mechanism also includes tabs 66 which extend radially inwardly from walls of the passageway 62 and distally toward the exit 68 of the passageway through the insert. When the catheter is passed through the insert in the direction indicated by arrow 70, the ends of the tabs 66 abut the catheter to frictionally engage the catheter to resist movement back into the receptacle. Although three tabs are shown in the figures, any suitable number can be provided.

Figure 8:
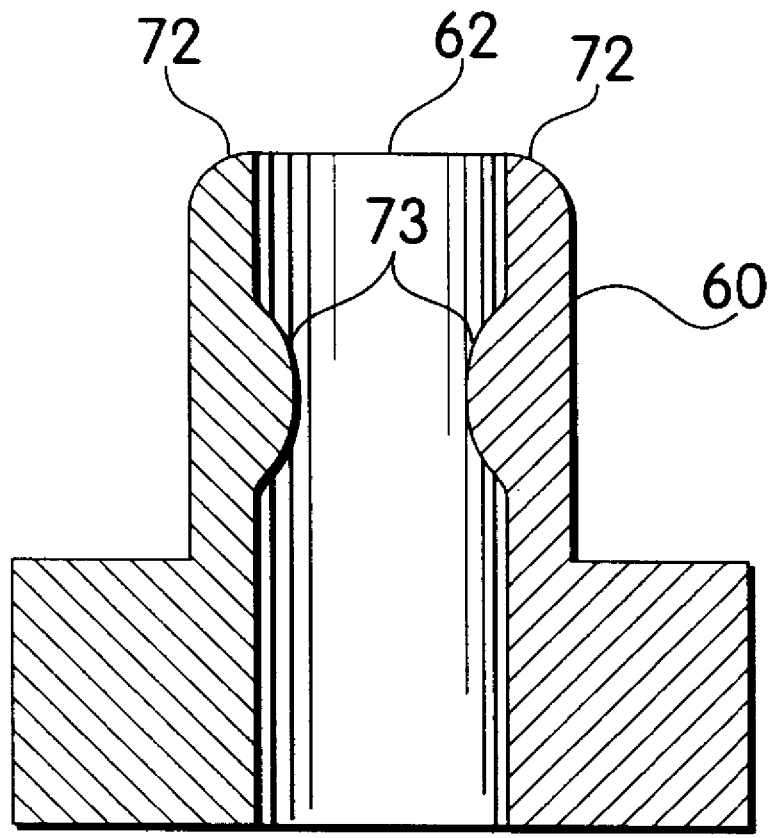
FIG. 8 is a cross-sectional view of a further embodiment of a catheter grasping mechanism.

In another embodiment, illustrated in FIG. 8, the walls 72 of the passageway 62 of the insert 60 are textured to provide a roughness which frictionally engages the catheter. The texture may comprise an all-over pattern or discrete protrusions 73 extending inwardly from walls of the passageway.

Figure 10:
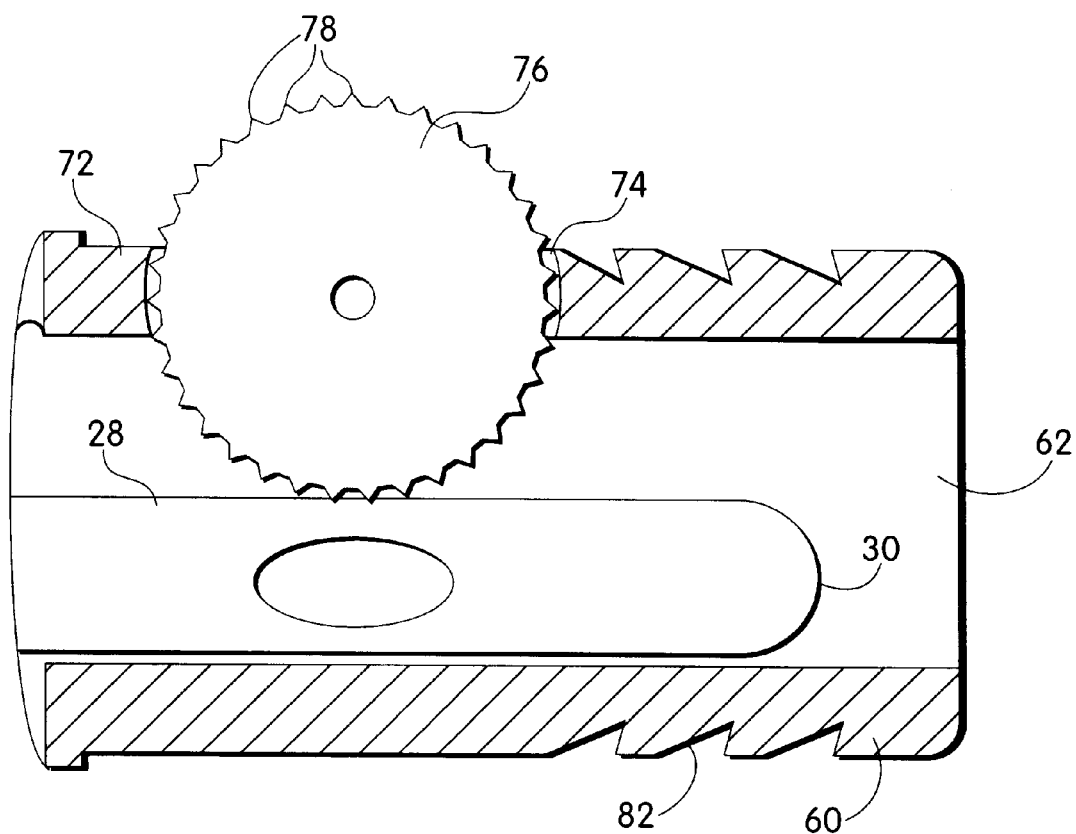
FIG. 10 is a cross-sectional view taken along lines A—A of FIG. 9.

In a further embodiment of the catheter grasping mechanism, illustrated in FIGS. 9 and 10, a slot or aperture 74 is formed through the wall 72 of the insert 60. A dial or gear 76 having outwardly extending teeth 78 is rotatably mounted in the slot in the insert. The dial protrudes through the slot to extend into the passageway 62 in the insert a distance sufficient to frictionally engage the teeth against the catheter. The dial also protrudes outside the insert, where a user's finger can rotate the dial to advance the catheter.

Figure 11:
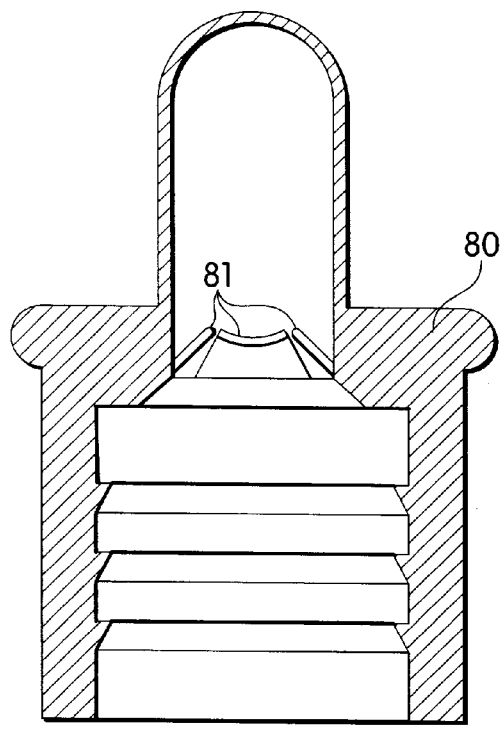
FIG. 11 is a side view of a further embodiment of a catheter grasping mechanism.
Figure 12:
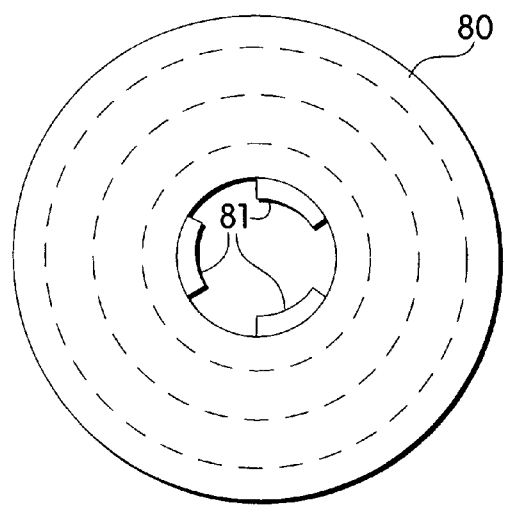
FIG. 12 is a plan view of the catheter grasping mechanism of FIG. 11.

As illustrated in FIG. 1, an introducer 80 to assist insertion of the catheter into the urethra may be placed over the insert 60, as is known in the art. The outer surface 82 of the insert 60 may be ribbed or otherwise textured to assist in frictionally retaining the introducer thereon (see particularly FIG. 10). A cap or cover 84 may be placed over the introducer during storage, also as known in the art. In another embodiment shown in FIGS. 11–12, a catheter grasping mechanism having tabs 81 or other protrusions such as described above with respect to the embodiments illustrated in FIGS. 5–8 can be formed within the introducer 80. Alternatively, the catheter can be grasped through the introducer by the user's fingers squeezing the introducer.

Finger holes 86, 88 are provided in the regions 90, 92 of the receptacle 12 adjacent the sides of the lubrication chamber 20. Preferably, one finger hole is provided in each side. The circumference of each finger hole may be reinforced in any suitable manner, such as by a bond line 94, which may be formed as the bond lines described above. The finger holes are particularly useful for self-catheterization. Although two finger holes are shown, it will be appreciated that a single finger hole or three or more finger holes could be provided if desired. Similarly, one or more finger holes can be provided in a receptacle that does not also include the lubrication chamber of the present invention.

In use, the user places a finger of one hand through each hole 86, 88 to suspend the receptacle 12. The remaining fingers of that hand can be used to hold the receptacle adjacent to the urethral opening. The other hand is free to manipulate the catheter 28 within the receptacle. The user grips the catheter through the flexible walls of the receptacle and threads the distal end 30 of the catheter through the passage 22 into the lubrication chamber 20 and out the exit 24.

In the lubrication chamber 20, the outer surface of the catheter 28 picks up a sufficient amount of lubricant 26 to ease insertion of the catheter into the urethra. By retaining the lubricant within the lubrication chamber separate from the main chamber, the walls of the receptacle do not stick together and it becomes easier for the user to manipulate the catheter through the receptacle walls.

Catheter advancement is achieved by gripping the catheter with a first hand through the receptacle walls and pushing it from the proximal end of the lubrication chamber. When the proximal end of the lubrication chamber reaches the distal end, the user releases the catheter. The user can retain the catheter in the advanced position by squeezing the catheter through the catheter grasping mechanism with the fingers of the other hand. The user can employ the fingers which extend through the two finger holes for this purpose. Alternatively, the catheter can be retained in the advanced position by the catheter engaging mechanism described above. The user then straightens out the receptacle with the first hand. Once the receptacle has been straightened out, the user grips the catheter through the walls of the receptacle again and advances it another distance until the proximal end of the lubrication chamber reaches the distal end. Additionally, compressing the lubrication chamber with each advance of the catheter acts as a pumping mechanism to force lubricant through the exit with the catheter. Once the distal end of the catheter reaches the patient's bladder, urine begins to flow and is collected in the main chamber of the receptacle.

Typically, the receptacle can hold up to 1200 cc of liquid, although receptacles having larger or smaller volumes can be provided. Indicia indicating the volume of urine collected may be marked along a wall of the receptacle. The catheter assembly of the present invention is applicable to all sizes of catheters, from 6 to 26 French, and can be used for adults, children, males, and females.

The invention is not to be limited by what has been particularly shown and described, except as indicated by the appended claims.

We claim:

1. A self-contained, self-lubricating catheter assembly comprising:

a receptacle comprising two opposed flexible, sheet-like walls extending from a closed distal end to a proximal end, a main chamber and a lubrication chamber formed between the flexible, sheet-like walls, a passage separating the main chamber and the lubrication chamber, and an exit from the lubrication chamber formed in the closed distal end of the walls of the receptacle;

a lubricating material disposed in the lubrication chamber; and a catheter disposed within the receptacle.

2. The catheter assembly of claim 1, wherein the passage between the lubrication chamber and the main chamber is sufficiently large to allow a catheter to pass therethrough and sufficiently narrow to minimize migration of the lubricating material from the lubrication chamber into the main chamber.

3. The catheter assembly of claim 1, wherein the receptacle further includes a catheter guideway disposed to direct the catheter toward the lubrication chamber.

4. The catheter assembly of claim 3, wherein the catheter guideway comprises a guide channel formed in a central region of the main chamber spaced from the lubrication chamber.

5. The catheter assembly of claim 1, further comprising a catheter grasping mechanism located within the exit, the catheter grasping mechanism having a passageway therethrough sized to allow the catheter to pass through.

6. The catheter assembly of claim 5, further comprising a catheter engaging device extending partially into the passageway and configured to permit advancement of the catheter out of the receptacle and resist movement of the catheter back into the receptacle.

7. The catheter assembly of claim 6, wherein the catheter engaging device comprises tabs extending radially inwardly and distally from walls of the passageway.

8. The catheter assembly of claim 6, wherein the catheter engaging device comprises protrusions extending inwardly from walls of the passageway.

9. The catheter assembly of claim 6, wherein the catheter engaging device comprises a dial rotatably mounted within an aperture in the catheter grasping mechanism, the dial having outwardly extending teeth disposed to protrude within the passageway to frictionally engage against the catheter and to extend outside the aperture for access by a user's finger.

10. The catheter assembly of claim 5, further comprising an introducer disposed over the catheter grasping mechanism.

11. The catheter assembly of claim 10, further comprising a cap disposed over the catheter grasping mechanism.

12. The catheter assembly of claim 10, further comprising a catheter engaging device extending partially into the introducer and configured to permit advancement of the catheter out of the receptacle and resist movement of the catheter back into the receptacle.

13. The catheter assembly of claim 1, further comprising a valve assembly disposed in the passage between the lubrication chamber and the main chamber.

14. A self-contained, self-lubricating catheter assembly comprising:

a receptacle comprising two opposed flexible walls extending from a closed distal end to a proximal end, a main chamber and a lubrication chamber formed between the flexible walls, a passage separating the main chamber and the lubrication chamber, and an exit from the lubrication chamber formed in the closed distal end of the receptacle, wherein the lubrication chamber is formed by bond lines sealing the opposed flexible walls;

a lubricating material disposed in the lubrication chamber; and a catheter disposed within the receptacle.

15. The catheter assembly of claim 14, wherein the bond lines are formed by heat sealing, adhesive, stitching, RF welding, impulse welding, or chemical bonding.

16. A self-contained, self-lubricating catheter assembly comprising:

a receptacle comprising two opposed flexible walls extending from a closed distal end to a proximal end, a main chamber and a lubrication chamber formed between the flexible walls, a passage separating the main chamber and the lubrication chamber, and an exit from the lubrication chamber formed in the closed distal end of the receptacle;

a lubricating material disposed in the lubrication chamber;

a catheter disposed within the receptacle; and a catheter guideway disposed to direct the catheter toward the lubrication chamber, the guideway comprising a guide channel formed in a central region of the main chamber spaced from the lubrication chamber, wherein the guide channel is formed by bond lines sealing the opposed flexible walls.

17. A self-contained, self-lubricating catheter assembly comprising:

a receptacle comprising two opposed flexible walls extending from a closed distal end to a proximal end, a main chamber and a lubrication chamber formed between the flexible walls, a passage separating the main chamber and the lubrication chamber, and an exit from the lubrication chamber formed in the closed distal end of the receptacle;

a lubricating material disposed in the lubrication chamber and a catheter disposed within the receptacle; and a catheter guideway disposed to direct the catheter toward the lubrication chamber, wherein the catheter guideway comprises bond lines sealing the opposed flexible walls and extending angularly from the lubrication chamber to sides of the receptacle.

18. A self-contained, self-lubricating catheter assembly comprising:

a receptacle comprising two opposed flexible walls extending from a distal end to a proximal end, a main chamber and a lubrication chamber formed between the flexible walls, a passage separating the main chamber and the lubrication chamber, and an exit from the lubrication chamber formed in the distal end of the receptacle;

a lubricating material disposed in the lubrication chamber;

a catheter disposed within the receptacle; and a finger hole disposed through the opposed flexible walls in a region adjacent to the distal end and on a side of the lubrication chamber.

19. The catheter assembly of claim 18, further comprising a further finger hole disposed through the opposed flexible walls in a further region adjacent the distal end and on an opposite side of the lubrication chamber from the finger hole.

20. The catheter assembly of claim 18, further comprising reinforcing around the finger opening.

21. The catheter assembly of claim 20, wherein the reinforcing comprises a bond line around the finger opening.

22. A self-contained catheter assembly comprising:

a receptacle comprising two opposed flexible walls extending from a proximal end to a distal end, and a chamber between the flexible walls;

a catheter, at least a portion of the catheter disposed within the chamber in the receptacle;

an exit formed in the distal end of the walls of the receptacle; and a catheter grasping mechanism located within the exit, the catheter grasping mechanism having a passageway therethrough sized to allow the catheter to pass through and operative to retain the catheter therein, and including a catheter engaging device extending partially into the passageway to permit advancement of the catheter out of the receptacle and resist movement of the catheter back into the receptacle.

23. The catheter assembly of claim 22, wherein the catheter engaging device comprises protrusions extending inwardly from walls of the passageway.

24. The catheter assembly of claim 22, wherein the catheter engaging device comprises tabs extending radially inwardly and distally from walls of the passageway.

25. The catheter assembly of claim 22, wherein the catheter grasping mechanism is sufficiently squeezable to allow the catheter to be retained therein by squeezing of a user's fingers.

26. The catheter assembly of claim 22, further comprising an introducer disposed over the catheter grasping mechanism.

27. The catheter assembly of claim 26, further comprising a cap disposed over the introducer.

28. A self contained catheter assembly comprising:

a receptacle comprising two opposed flexible walls extending from a proximal end to a distal end, and a chamber between the flexible walls;

a catheter, at least a portion of the catheter disposed within the chamber in the receptacle;

an exit formed in the distal end of the receptacle;

a catheter grasping mechanism located within the exit, the catheter grasping mechanism having a passageway therethrough sized to allow the catheter to pass through and including a catheter engaging device extending partially into the passageway, wherein the catheter engaging device comprises a dial rotatably mounted within an aperture in the catheter grasping mechanism and configured to permit advancement of the catheter out of the receptacle and resist movement of the catheter back into the receptacle, the dial having outwardly extending teeth disposed to protrude within the passageway to frictionally engage against the catheter and to extend outside the aperture for access by a user's finger.

29. A self-contained catheter assembly comprising:

a receptacle comprising two opposed flexible walls extending from a proximal end to a sealed distal end, and a chamber between the flexible walls, wherein the chamber comprises a main chamber and a lubrication chamber defined by bond lines sealing the opposed flexible walls, and a lubricating material is disposed in the lubrication chamber;

a catheter, at least a portion of the catheter disposed within the chamber in the receptacle;

an exit formed in the distal end of the receptacle; and a catheter grasping mechanism located within the exit and fixed to the sealed distal end, the catheter grasping mechanism having a passageway therethrough sized to allow the catheter to pass through and operative to retain the catheter therein.

30. A self-contained catheter assembly comprising:

a receptacle comprising two opposed flexible walls extending from a proximal end to a distal end, and a chamber between the flexible walls, the opposed walls comprising a further portion adjacent to the chamber and the distal end, and a finger hole disposed through the further portion of the opposed walls;

a catheter, at least a portion of the catheter disposed within the chamber in the receptacle;

an exit formed in the distal end of the receptacle; and a catheter grasping mechanism located within the exit, the catheter grasping mechanism having a passageway therethrough sized to allow the catheter to pass through and operative to retain the catheter therein.

31. A prelubricated, self-contained catheter assembly comprising:

a receptacle having two opposed flexible walls extending from a proximal end to a distal end, a chamber defined between a portion of the opposed walls, at least a further portion of the opposed walls adjacent the chamber, at least one finger hole disposed through the further portion of the opposed walls;

an exit from the chamber formed in the distal end of the receptacle; and a catheter, at least a portion of the catheter disposed within the receptacle.

32. The catheter assembly of claim 31, wherein the chamber is defined by bond lines sealing the opposed flexible walls.

33. The catheter assembly of claim 31, wherein the chamber comprises a main chamber and a lubrication chamber defined by bond lines sealing the opposed flexible walls, and a lubricating material disposed in the lubrication chamber.

34. The catheter assembly of claim 31, further comprising two finger holes disposed on opposed sides of the lubrication chamber.

35. The catheter assembly of claim 31, further comprising reinforcing around the finger opening.

36. The catheter assembly of claim 35, wherein the reinforcing comprises a bond line around the finger opening.

37. The catheter assembly of claim 31, further comprising a catheter grasping mechanism located proximate the exit, the catheter grasping mechanism having a passageway therethrough sized to allow the catheter to pass through.

38. The catheter assembly of claim 37, further comprising a catheter engaging device extending partially into the passageway and configured to permit advancement of the catheter out of the receptacle and resist movement of the catheter back into the receptacle.

* * * * *